United States Patent
Nishijima

(10) Patent No.: US 12,154,678 B2
(45) Date of Patent: Nov. 26, 2024

(54) X-RAY CT APPARATUS AND DATA TRANSFER METHOD

(71) Applicant: CANON MEDICAL SYSTEMS CORPORATION, Otawara (JP)

(72) Inventor: Akira Nishijima, Nasushiobara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 484 days.

(21) Appl. No.: 17/461,030

(22) Filed: Aug. 30, 2021

(65) Prior Publication Data

US 2022/0068465 A1    Mar. 3, 2022

(30) Foreign Application Priority Data

Aug. 31, 2020  (JP) ................................ 2020-145782
Aug. 31, 2020  (JP) ................................ 2020-146297

(51) Int. Cl.
G16H 30/20          (2018.01)
A61B 6/00           (2024.01)
G16H 50/20          (2018.01)

(52) U.S. Cl.
CPC .............. G16H 30/20 (2018.01); A61B 6/54 (2013.01); G16H 50/20 (2018.01)

(58) Field of Classification Search
CPC ........ G16H 30/20; G16H 50/20; G16H 10/60; G16H 40/63; A61B 6/54; A61B 6/035; A61B 6/4208; A61B 6/44; A61B 6/4429; A61B 6/481
See application file for complete search history.

(56) References Cited

U.S. PATENT DOCUMENTS

| | | | | |
|---|---|---|---|---|
| 4,494,141 A | * | 1/1985 | Altekruse | G06T 11/005 378/19 |
| 4,847,765 A | * | 7/1989 | Nonnweiler | H05G 1/30 700/1 |
| 5,090,040 A | * | 2/1992 | Lanza | G06T 1/60 378/53 |
| 6,266,387 B1 | * | 7/2001 | Gscheidmeier | A61B 6/032 378/116 |
| 6,560,307 B2 | * | 5/2003 | Marume | G06T 1/00 378/4 |

(Continued)

FOREIGN PATENT DOCUMENTS

JP  5-89006 U  12/1993
JP  2005-204258 A  7/2005

(Continued)

OTHER PUBLICATIONS

Japanese Office Action issued Jan. 16, 2024 in Japanese Application 2020-145782, 2 pages.

(Continued)

*Primary Examiner* — Christine S. Kim
(74) *Attorney, Agent, or Firm* — Oblon, McClelland, Maier & Neustadt, L.L.P.

(57) ABSTRACT

An X-ray CT apparatus according to an embodiment includes a buffer and a processing circuitry. The buffer temporarily stores therein data detected by an X-ray detector. The processing circuitry controls transfer of the data in units of a scan, the data being acquired by each scan of a scan plan constituted of a plurality of scans.

23 Claims, 11 Drawing Sheets

(56) References Cited

U.S. PATENT DOCUMENTS

| | | | |
|---|---|---|---|
| 7,254,210 B2* | 8/2007 | Popescu | A61B 6/032 378/19 |
| 8,406,537 B2* | 3/2013 | Breuer | A61B 6/56 378/19 |
| 2009/0169119 A1* | 7/2009 | Wegener | H04N 19/152 382/128 |
| 2011/0286574 A1 | 11/2011 | Suzuki | |
| 2014/0231663 A1* | 8/2014 | Geisslinger | G06F 9/30 250/336.1 |

FOREIGN PATENT DOCUMENTS

| | | |
|---|---|---|
| JP | 2009-131614 A | 6/2009 |
| JP | 2011-172603 A | 9/2011 |
| JP | 2013-230315 A | 11/2013 |
| JP | 5611667 B2 | 10/2014 |
| JP | 2016-97088 A | 5/2016 |
| JP | 2018-550 A | 1/2018 |

OTHER PUBLICATIONS

Japanese Office Action issued Jan. 16, 2024 in Japanese Application 2020-146297, 2 pages.

* cited by examiner

X-RAY CT APPARATUS AND DATA TRANSFER METHOD

CROSS-REFERENCE TO RELATED APPLICATIONS

This application is based upon and claims the benefit of priority from Japanese Patent Applications No. 2020-145782 and No. 2020-146297, both filed on Aug. 31, 2020, the entire contents of all of which are incorporated herein by reference.

FIELD

Embodiments described herein relate generally to an X-ray CT apparatus and a data transfer method.

BACKGROUND

One of objects of embodiments disclosed in the present specification and the drawings is to scan a subject while preventing a storage capacity of a buffer from being increased. However, the objects of the embodiments disclosed in the present specification and the drawings are not limited to the object described above. An object corresponding to an effect of each configuration described in the embodiments (described later) can be assumed to be another object.

DETAILED DESCRIPTION

Figure 1:
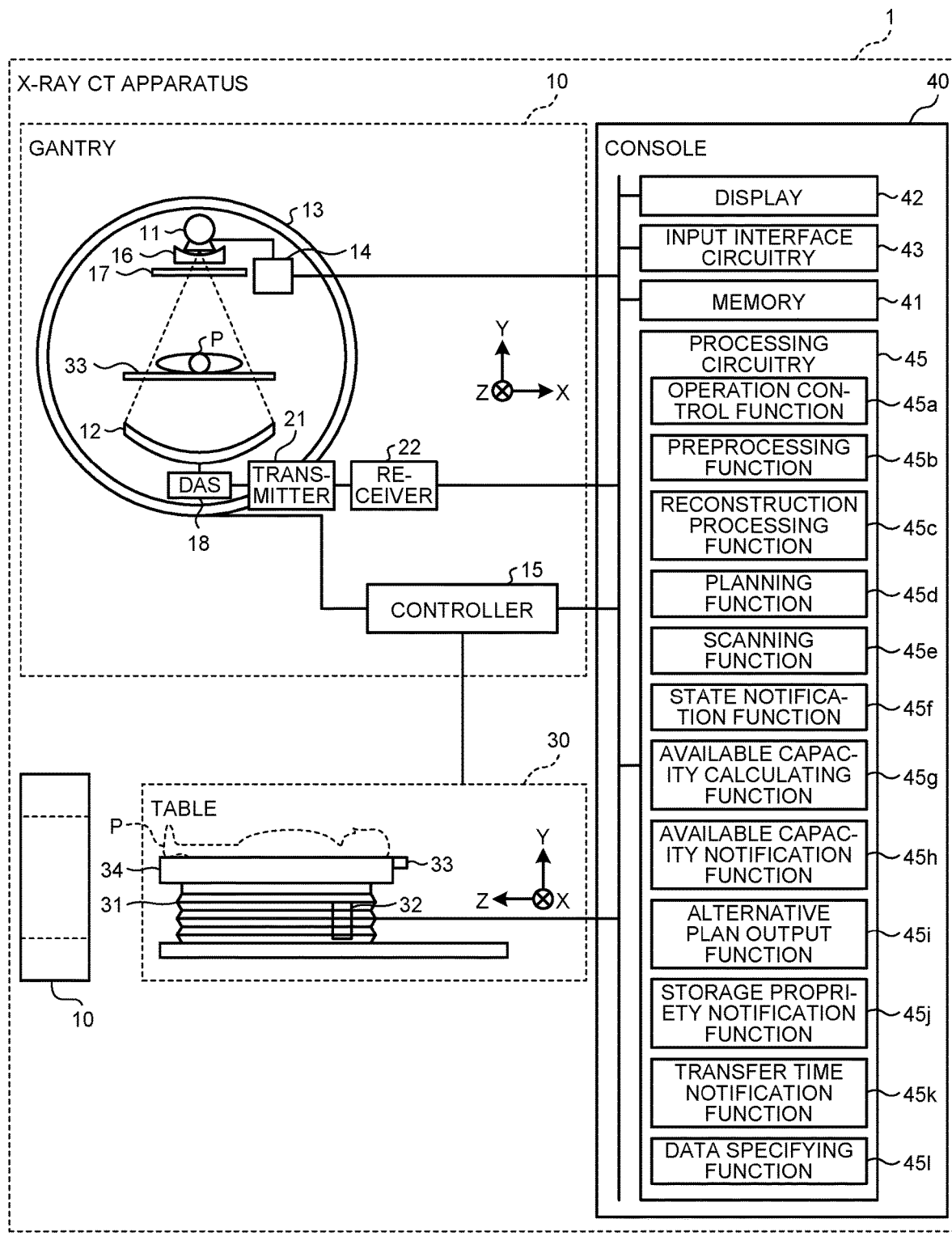
FIG. 1 is a block diagram illustrating an example of a configuration of an X-ray CT apparatus according to a first embodiment.

The following describes an X-ray CT apparatus and a data transfer method according to embodiments with reference to the drawings. In the following embodiments, parts denoted by the same reference numerals are assumed to similarly operate, and redundant description will be appropriately omitted.

First Embodiment

FIG. 1 is a block diagram illustrating an example of a configuration of an X-ray CT apparatus 1 according to a first embodiment. The X-ray CT apparatus 1 is an image diagnostic apparatus that includes an X-ray detector 12 having high resolution, and acquires a high-definition image. The X-ray CT apparatus 1 includes a gantry 10, a table 30, and a console 40. The gantry 10 transfers data that is acquired by scanning a subject P to the console 40. The console 40 then reconstructs the data received from the gantry 10 to generate CT image data.

The X-ray CT apparatus 1 includes the X-ray detector 12 having high resolution, so that a data amount of acquired data is increased. As the data amount is increased, in the X-ray CT apparatus 1, an acquisition rate of the data that is acquired per unit time may exceed a transfer rate of the data in some cases. However, when the acquisition rate is lowered corresponding to the transfer rate, it takes long time to scan the subject P by the X-ray CT apparatus 1. Thus, the X-ray CT apparatus 1 temporarily stores the acquired data in a buffer, and transfers the data stored in the buffer. Due to this, the X-ray CT apparatus 1 can transfer the acquired data without lowering the acquisition rate.

The X-ray CT apparatus 1 has various imaging protocols. The amount of data to be acquired is different depending on the imaging protocol. To store all pieces of the data acquired by using the imaging protocol with which the data amount becomes the largest, the X-ray CT apparatus 1 is required to include a buffer having a large storage capacity. On the other hand, there is a demand for reducing the storage capacity of the buffer in view of heat generation, power consumption, a mounting area, production cost, and the like.

However, when the storage capacity of the buffer is reduced, the storage capacity of the buffer may become insufficient. When the storage capacity of the buffer becomes insufficient, the X-ray CT apparatus 1 needs to stop scanning of the subject P to prevent the data from being overwritten. However, the X-ray CT apparatus 1 cannot stop scanning of the subject P in some cases. For example, when scanning of the subject P is stopped in a case of scanning the subject P by injecting a contrast medium, the X-ray CT apparatus 1 cannot perform intended imaging because the contrast medium flows. Thus, there is a demand for a technique of scanning the subject P while preventing the storage capacity of the buffer from being increased.

The following exemplifies a case in which the first embodiment is applied to the X-ray CT apparatus 1 for acquiring a high-definition image. However, the X-ray CT apparatus 1 may be an apparatus that acquires data using a Photon Counting (PC) method, or may be an apparatus that acquires data using another method.

In the first embodiment, a rotation axis of a rotation frame 13 in a non-tilted state or a longitudinal direction of a tabletop 33 of the table 30 is defined as a Z-axis direction, an axis direction that is orthogonal to the Z-axis direction and horizontal to a floor surface is defined as an X-axis direction, and an axis direction that is orthogonal to the Z-axis direction and perpendicular to the floor surface is defined as a Y-axis direction.

The gantry 10 includes an imaging system for imaging a medical image used for a diagnosis. That is, the gantry 10 is an apparatus including the imaging system that emits X-rays to the subject P and collects projection data from detection data of the X-rays transmitted through the subject P, and includes an X-ray tube 11, a wedge 16, a collimator 17, the X-ray detector 12, an X-ray high voltage circuitry 14, a data acquisition system (DAS) 18, the rotation frame 13, a controller 15, and the table 30.

The X-ray tube 11 is a vacuum tube that emits thermos electrons from a cathode (filament) toward an anode (target) when a high voltage is applied from the X-ray high voltage circuitry 14.

The wedge 16 is a filter for adjusting an X-ray dose of the X-rays emitted from the X-ray tube 11. Specifically, the wedge 16 is a filter that transmits and attenuates the X-rays emitted from the X-ray tube 11 so that the X-rays emitted from the X-ray tube 11 to the subject P are distributed in a predetermined state.

The wedge 16 is, for example, a wedge filter or a bow-tie filter, and is a filter obtained by processing aluminum to have a predetermined target angle or a predetermined thickness.

The collimator 17 is a lead plate and the like for narrowing an irradiation range of the X-rays transmitted through the wedge 16, and a slit is formed by combining a plurality of lead plates and the like.

The X-ray detector 12 detects the X-rays that are emitted from the X-ray tube 11 and have passed through the subject P, and outputs an electric signal corresponding to the X-ray dose to a data collection circuitry (the DAS 18). The X-ray detector 12 includes a plurality of X-ray detection element arrays in which a plurality of X-ray detection elements are arranged in a channel direction along one circular arc centered on a focal point of the X-ray tube 11, for example. The X-ray detector 12 has a structure in which a plurality of X-ray detection element arrays are arranged in a slice direction (also referred to as a body axis direction or a column direction), the X-ray detection element arrays in which the X-ray detection elements are arranged in the channel direction.

The X-ray detector 12 is, for example, a detector of an indirect conversion type including a grid, a scintillator array, and an optical sensor array. The scintillator array includes a plurality of scintillators, and the scintillator includes a scintillator crystal that outputs light having a photon quantity corresponding to an X-ray incident amount. The grid is arranged on a surface on an X-ray incident side of the scintillator array, and includes an X-ray shielding plate having a function of absorbing scattered X-rays. The optical sensor array has a function of converting the X-ray into an electric signal corresponding to an amount of light from the scintillator, and includes an optical sensor such as a photomultiplier tube (PMT), for example. The X-ray detector 12 may also be a detector of a direct conversion type including a semiconductor element that converts the incident X-ray into an electric signal.

The X-ray high voltage circuitry 14 includes an electric circuit such as a transformer and a rectifier, a high voltage generation circuitry having a function of generating a high voltage to be applied to the X-ray tube 11, and an X-ray controller that controls an output voltage corresponding to the X-ray emitted from the X-ray tube 11. The high voltage generation circuitry may be a transformer type, or may be an inverter type. The X-ray high voltage circuitry 14 may be arranged on the rotation frame 13, or may be arranged on a fixed frame (not illustrated) side of the gantry 10. The fixed frame is a frame that supports the rotation frame 13 in a rotatable manner.

Figure 3:
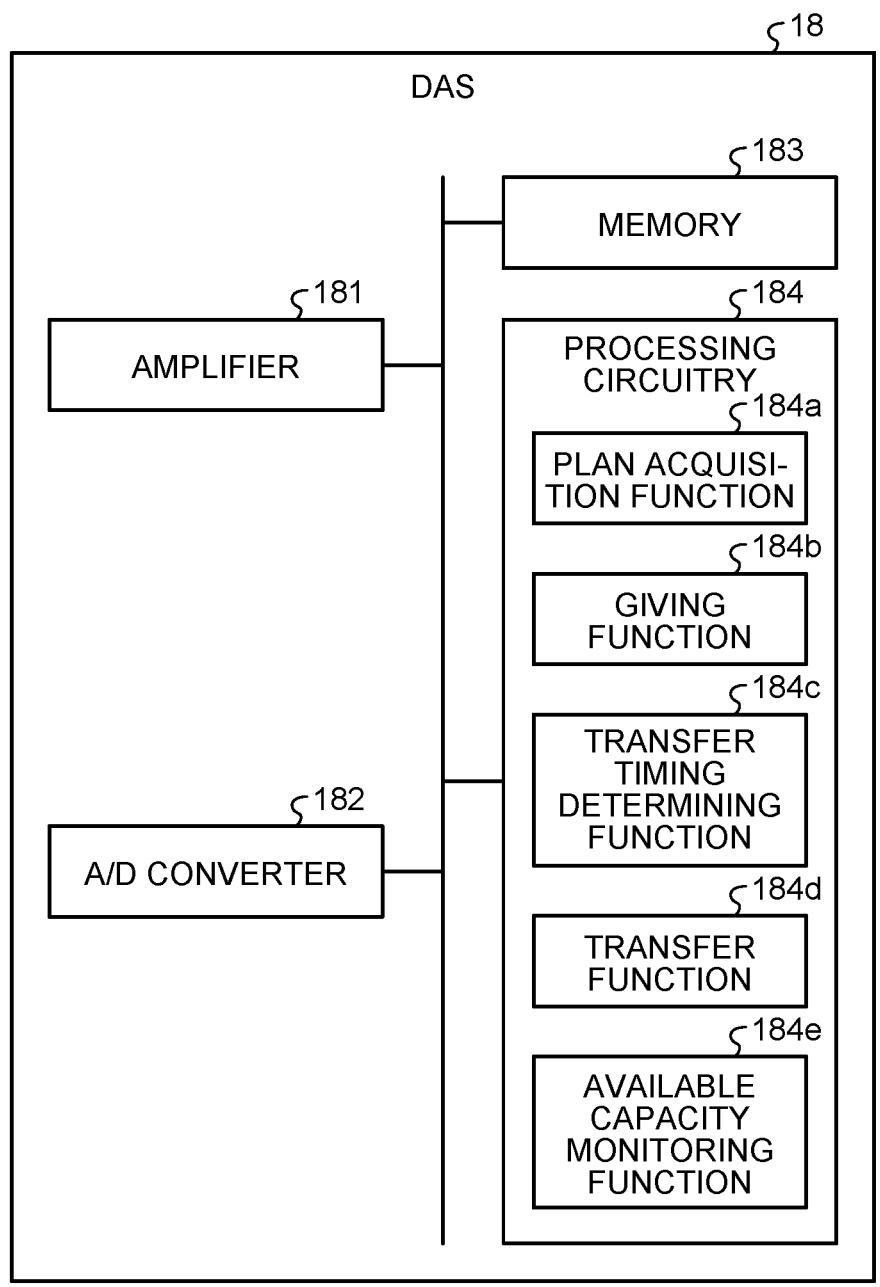
FIG. 3 is a block diagram illustrating an example of a configuration of a DAS according to the first embodiment.

The DAS 18 acquires detection data based on the electric signal output from each of the X-ray detection elements of the X-ray detector 12. The detection data acquired by the DAS 18 is transferred to the console 40. With reference to FIG. 3, a detailed configuration of the DAS 18 will be described later.

The detection data is a general term of the data that is acquired by the DAS 18 based on the electric signal output from the X-ray detector 12. A set of one or more pieces of scan data included in the same scan plan in the detection data is referred to as a scan data set. The scan plan is a plan for a scan for the subject P designated by the imaging protocol, and includes one or more scans. The scan in the present embodiment means a series of operations of repeatedly performing X-ray irradiation and X-ray detection at successive projection positions (view numbers). Thus, in a case in which the view number is reset, and X-ray irradiation and X-ray detection are repeatedly performed with new successive view numbers, it can be said that a different scan is performed. The scan data is, for example, a set of data that is acquired by a series of scans to which successive numbers are given as the view numbers indicating the projection positions. The scan data is not only classified in units of a scan, but can also be a group of data among a plurality of optional pieces of data obtained by dividing the scan data set.

The rotation frame 13 is a frame having an annular shape that supports the X-ray tube 11 and the X-ray detector 12 to be opposed to each other, and causes the X-ray tube 11 and the X-ray detector 12 to rotate by the controller 15. The rotation frame 13 may further support the X-ray high voltage circuitry 14 and the DAS 18 in addition to the X-ray tube 11 and the X-ray detector 12. By way of example, the detection data acquired by the DAS 18 is transmitted from a transmitter 21 including a light emitting diode arranged on the rotation frame 13 to a receiver 22 including a photodiode arranged on a non-rotation portion of the gantry 10 such as the fixed frame by optical communication, and transferred to the console 40. A method of transmitting the detection data from the rotation frame 13 to the non-rotation portion of the gantry 10 is not limited to optical communication, and another non-contact type data transmission method may be used.

The controller 15 includes a processing circuitry including a CPU and the like, and a driving mechanism such as a motor and an actuator. The controller 15 has a function of performing operation control for the gantry 10 and the table 30 by receiving an input signal from an input interface circuitry 43 attached to the console 40 or an input interface circuitry attached to the gantry 10. The controller 15 also performs control for causing the rotation frame 13 to rotate by receiving an input signal, or performs control for causing the gantry 10 and the table 30 to operate.

For example, the controller 15 causes the rotation frame 13 to rotate about an axis parallel with the X-axis direction to tilt the gantry 10 based on inclination angle (tilt angle) information input via the input interface circuitry attached to the gantry 10.

The table 30 is an apparatus on which the subject P as a scanning target is placed to be moved, and includes a base 31, a table drive circuitry 32, the tabletop 33, and a support frame 34. The base 31 is a housing that supports the support frame 34 to be movable in a vertical direction. The table drive circuitry 32 is a motor or an actuator that moves the tabletop 33 on which the subject P is placed in a major axis direction (Z-axis direction in FIG. 1) thereof. The tabletop 33 arranged on an upper surface of the support frame 34 is a plate on which the subject P is placed. The table drive circuitry 32 may also move the support frame 34 in the major axis direction of the tabletop 33 in addition to the tabletop 33.

The table drive circuitry 32 moves the base 31 in an upper and lower direction in accordance with a control signal from the controller 15. The table drive circuitry 32 moves the tabletop 33 in the major axis direction in accordance with the control signal from the controller 15.

The console 40 is an apparatus that receives an operation on the X-ray CT apparatus 1 by a user, and reconstructs X-ray CT image data from the detection data collected by the gantry 10. The console 40 includes a memory 41, a display 42, an input interface circuitry 43, and a processing circuitry 45.

For example, the memory 41 is implemented by a semiconductor memory element such as a random access memory (RAM) and a flash memory, a hard disk, an optical disc, and the like. The memory 41 stores, for example, projection data and reconstructed image data. The memory 41 stores therein scan data transferred from the DAS 18. The memory 41 is an example of a storage circuitry.

The memory 41 also stores therein dedicated programs for implementing an operation control function 45a, a preprocessing function 45b, a reconstruction processing function 45c, a planning function 45d, a scanning function 45e, a state notification function 45f, an available capacity calculating function 45g, an available capacity notification function 45h, an alternative plan output function 45i, a storage propriety notification function 45j, a transfer time notification function 45k, and a data specifying function 45l(described later).

The display 42 is a monitor referred to by the user, and displays various kinds of information. For example, the display 42 outputs a medical image (CT image) generated by the processing circuitry 45, a graphical user interface (GUI) for receiving various operations from the user, and the like. For example, the display 42 is a liquid crystal display or a cathode ray tube (CRT) display.

The input interface circuitry 43 receives various input operations from the user, and converts the received input operations into electric signals to be output to the processing circuitry 45. For example, the input interface circuitry 43 receives, from the user, a collecting condition for collecting projection data, a reconstruction condition for reconstructing a CT image, an image processing condition for generating a postprocessing image from the CT image, and the like. For example, the input interface circuitry 43 is implemented by a mouse, a keyboard, a trackball, a switch, a button, a joystick, and the like.

The processing circuitry 45 controls an operation of the entire X-ray CT apparatus 1. The processing circuitry 45 has, for example, the operation control function 45a, the preprocessing function 45b, the reconstruction processing function 45c, the planning function 45d, the scanning function 45e, the state notification function 45f, the available capacity calculating function 45g, the available capacity notification function 45h, the alternative plan output function 45i, the storage propriety notification function 45j, the transfer time notification function 45k, and the data specifying function 45l. In the embodiment, respective processing functions executed by the operation control function 45a, the preprocessing function 45b, the reconstruction processing function 45c, the planning function 45d, the scanning function 45e, the state notification function 45f, the available capacity calculating function 45g, the available capacity notification function 45h, the alternative plan output function 45i, the storage propriety notification function 45j, the transfer time notification function 45k, and the data specifying function 45l as constituent elements are stored in the memory 41 in a form of computer-executable program. The processing circuitry 45 is a processor that implements a function corresponding to each computer program by reading out and executing the computer program from the memory 41. In other words, the processing circuitry 45 that has read out each computer program is assumed to have each function indicated in the processing circuitry 45 in FIG. 1.

Regarding FIG. 1, it is assumed that a single processor implements the operation control function 45a, the preprocessing function 45b, the reconstruction processing function 45c, the planning function 45d, the scanning function 45e, the state notification function 45f, the available capacity calculating function 45g, the available capacity notification function 45h, the alternative plan output function 45i, the storage propriety notification function 45j, the transfer time notification function 45k, and the data specifying function 45l. Alternatively, the processing circuitry 45 may be configured by combining a plurality of independent processors, and each of the processors may execute the computer program to implement the function. Regarding FIG. 1, it is assumed that a single storage circuit such as the memory 41 stores therein the computer program corresponding to each of the processing functions. Alternatively, a plurality of storage circuits may be arranged in a distributed manner, and the processing circuitry 45 may be configured to read out a corresponding computer program from an individual storage circuit.

A word of "processor" used in the above description means, for example, a central processing unit (CPU), a graphical processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). The processor implements the function by reading out and executing the computer program stored in the memory 41. The configuration may be made such that the computer program is directly incorporated in a circuit of the processor instead of being stored in the memory 41. In this case, the processor implements the function by reading out and executing the computer program incorporated in the circuit.

The operation control function 45a controls various functions of the processing circuitry 45 based on an input operation that is received from the user via the input interface circuitry 43. For example, the operation control function 45a receives inputs of user information for a login (for example, a user ID and the like), subject information, and the like via the input interface circuitry 43. The operation control function 45a also receives an input of the imaging protocol as content of a scan to be performed on the subject P. The operation control function 45a is an example of an input unit. The processing circuitry 45 performs control related to imaging for positioning, main imaging, and the like by the operation control function 45a.

The preprocessing function 45b generates data obtained by performing preprocessing such as logarithm conversion processing, offset processing, sensitivity correction processing between channels, or beam hardening correction on the detection data output from the DAS 18. The data before preprocessing (detection data) and the data after preprocessing may be collectively referred to as projection data in some cases.

The reconstruction processing function 45c performs reconstruction processing on the projection data generated by the preprocessing function 45b using a filtered back projection method, a successive approximation reconstruction method, and the like in accordance with the reconstruction condition, and generates CT image data.

The reconstruction processing function 45c converts the reconstructed CT image data into tomogram data of an optional cross section or three-dimensional image data using a well-known method based on the input operation that is received from the user via the input interface circuitry 43.

The planning function 45d generates the scan plan and the transfer plan. The transfer plan is information indicating a procedure of transferring scan data that is acquired by a scan indicated by the scan plan. That is, the transfer plan indicates the order of transferring the scan data, and a trigger for transferring each piece of the scan data.

More specifically, the planning function 45d generates the scan plan based on the imaging protocol, and information about residual capacity of a memory 183 of the DAS 18 before the scan indicated by the scan plan is performed.

Specifically, the planning function 45d acquires the information about the residual capacity of the memory 183 before the scan indicated by the scan plan is performed. The information about the residual capacity of the memory 183 is information indicating a residual available capacity of the memory 183 into which data can be written. For example, the planning function 45d may acquire the information by storing the information about the residual capacity of the memory 183 that is acquired by the available capacity notification function 45h at the time when a previous scan is performed, or may acquire the information from the available capacity calculating function 45g or an available capacity monitoring function 184e as occasion demands.

The planning function 45d generates the scan plan indicating a procedure of scanning instructed by the imaging protocol. The planning function 45d is an example of a plan generation unit. In other words, the planning function 45d generates the scan plan to cause the scan designated by the imaging protocol to be performed in the order designated by the imaging protocol. However, the memory 183 (refer to FIG. 3) of the DAS 18 overflows when an amount of acquired scan data exceeds the available capacity. Thus, the planning function 45d determines a timing for performing the scan to prevent the memory 183 from overflowing. The planning function 45d then generates the scan plan indicating the scan designated by the imaging protocol, and the trigger for performing the scan.

In a case in which an interrupt of the scan plan is designated, the planning function 45d generates a scan plan for causing the scan indicated by the imaging protocol of an interruption target to be performed earlier. For example, the interrupt of the scan plan is designated in a case in which an emergency case occurs.

The planning function 45d also generates the transfer plan indicating a plan for transferring the scan data stored in the memory 183 to the console 40. The planning function 45d is an example of a generation unit. More specifically, the planning function 45d generates the transfer plan indicating a transfer timing based on the scan plan, the information about the residual capacity of the memory 183, and a transfer speed of the scan data from the memory 183 of the DAS 18 to the memory 41 of the console 40.

The planning function 45d generates the transfer plan for transferring the scan data to the console 40 basically in the order of being scanned. However, when the scan data is transferred in the order of being scanned, a waiting time of the user may be caused in some cases. In such a case, the planning function 45d generates the transfer plan for transferring the scan data in an order different from the order of being scanned indicated by the scan plan. For example, in a case in which the scan data having a small data amount is transmitted subsequently to the scan data having a large data amount, and the scan data having a large data amount cannot be transferred within the next transfer time, the planning function 45d generates the transfer plan for transferring the scan data having a small data amount earlier.

The planning function 45d also changes the order not only for the scan data in the same scan plan but also for the scan data in a different scan plan. For example, the planning function 45d generates the transfer plan for transferring the scan data in a scan plan as a latecomer earlier. That is, the planning function 45d generates the transfer plan for transferring the scan data of the scan plan that has been performed earlier after transferring the scan data acquired by the scan plan that has been performed later under the condition that, among a plurality of the scan plans, the data amount of the scan data acquired by the scan plan to be executed later is smaller than available capacity of the memory 183 of the DAS 18. Due to this, in a case in which it takes long time for transferring the scan data of the scan plan that has been performed earlier, the planning function 45d can reduce the waiting time of the user of the scan plan that has been executed later by transferring the scan data of the scan plan that has been executed later earlier.

In a case in which an interrupt of the scan plan is designated, the planning function 45d generates the transfer plan again, the transfer plan including the imaging protocol of the interruption target. For example, the planning function 45d generates the transfer plan for resuming transfer of the scan data after the scan data of the scan plan as the interruption target is completely transferred.

Figure 2:
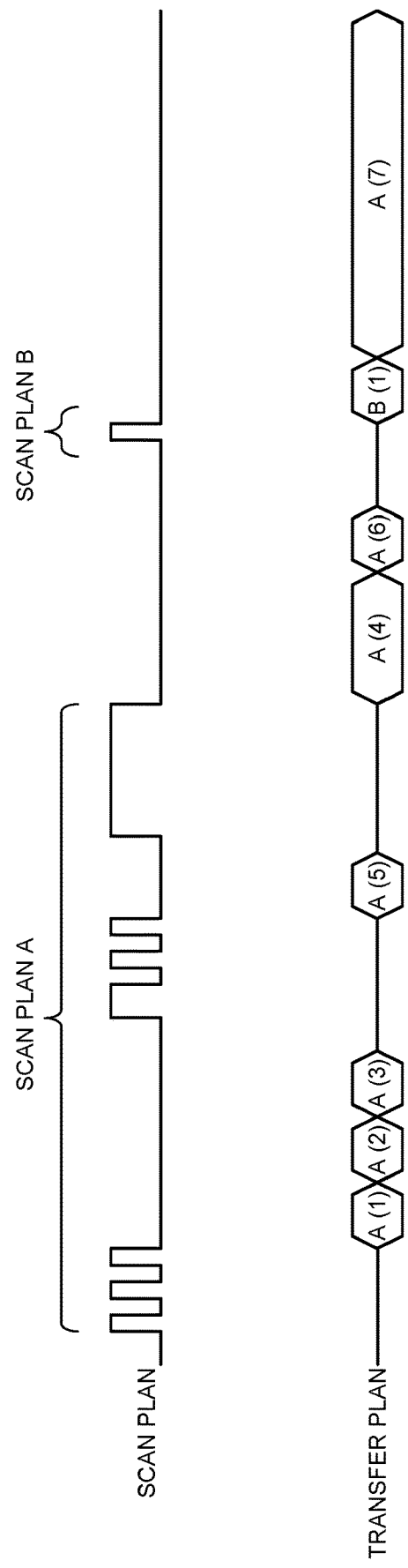
FIG. 2 is a timing chart illustrating an example of a scan plan and a transfer plan.

The following exemplifies the scan plan and the transfer plan generated by the planning function 45d. FIG. 2 is a timing chart illustrating an example of the scan plan and the transfer plan. The scan plan illustrated in FIG. 2 indicates that a scan plan B for performing one scan designated by the imaging protocol is performed after a scan plan A for performing seven scans designated by the imaging protocol. The transfer plan illustrated in FIG. 2 indicates that the first scan data, the second scan data, and the third scan data of the scan plan A are transferred in this order triggered by completion of the third scan of the scan plan A. The transfer plan illustrated in FIG. 2 indicates that the fifth scan data is transferred triggered by completion of the sixth scan of the scan plan A.

The transfer plan illustrated in FIG. 2 indicates that the fourth scan data and the sixth scan data are transferred triggered by completion of the seventh scan of the scan plan A. In this way, the transfer plan illustrated in FIG. 2 indicates that the fourth scan data is transferred after the fifth scan data of the scan plan A is transferred. A scanning time for the fourth scan is long, and the data amount of the scan data is large. Thus, the X-ray CT apparatus 1 cannot completely transfer the fourth scan data within a time between the sixth scan and the seventh scan. Thus, the planning function 45d improves efficiency in data transfer by transferring the fifth scan data. That is, the planning function 45d reduces the amount of data that should be transferred after the seventh scan.

In the transfer plan illustrated in FIG. 2, the seventh scan data of the scan plan A is transferred after the first scan data of the scan plan B is transferred triggered by completion of the first scan of the scan plan B. The scanning time for the seventh scan of the scan plan A is long, and the data amount of the scan data is large. Thus, when the first scan data of the scan plan B is transferred after the seventh scan data of the scan plan A is transferred, the user is caused to wait for a long time although the data amount of the subject P of the scan plan B is small. Thus, the planning function 45*d* reduces the waiting time of the user for the X-ray CT apparatus 1 by transferring the first scan data of the scan plan B earlier.

The scanning function 45*e* instructs to perform the scan of the subject P based on the scan plan. More specifically, the scanning function 45*e* instructs the gantry 10 to perform the scan having content indicated by the scan plan based on the trigger indicated by the scan plan. Due to this, the DAS 18 collects the scan data.

The state notification function 45*f* notifies the DAS 18 of a state of the scan. That is, the state notification function 45*f* issues a notification of a start of the scan and an end of the scan. The state notification function 45*f* also issues a notification of the scan plan and the transfer plan generated by the planning function 45*d*. Due to this, by counting the number of the scan being performed, the DAS 18 can grasp the scan plan and the number of the scan of the scan data being collected. The DAS 18 can also transfer the scan data based on the trigger indicated by the transfer plan.

The state notification function 45*f* may also notify the DAS 18 of the scan plan and the number of the scan being performed in place of the scan plan. Due to this notification, the DAS 18 can specify the number and the scan plan of the scan. Furthermore, the state notification function 45*f* may notify the DAS 18 of the scan plan and the number of the scan to be transferred in place of the transfer plan. Due to this, the DAS 18 can transfer the designated scan data at the transfer timing indicated by the transfer plan.

In a case in which an interrupt of a scan plan is designated, the state notification function 45*f* may notify the DAS 18 of suspension of transfer of the scan data in the middle of transfer. Due to this, the DAS 18 is enabled to transfer the scan data of the scan plan as the interruption target earlier.

The available capacity calculating function 45*g* calculates the residual capacity of the memory 183 of the DAS 18 for storing therein the scan data based on the scan plan and the transfer plan. The scan plan indicates a procedure of the scan to be performed for the subject P. In other words, the scan plan indicates content of the scan to be performed for the subject P, and a timing at which the scan data is stored in the memory 183 of the DAS 18. Thus, the available capacity calculating function 45*g* calculates a data amount that is acquired in a case in which the scan indicated by the scan plan is performed. The available capacity calculating function 45*g* is an example of a calculation unit.

The transfer plan indicates a timing at which the scan data is transferred from the memory 183 of the DAS 18. In other words, the transfer plan indicates a timing at which the scan data is read out from the memory 183 of the DAS 18. Thus, the available capacity calculating function 45*g* calculates the residual capacity of the memory 183 for storing therein the scan data at each timing.

The available capacity calculating function 45*g* can calculate the residual capacity of the memory 41 for storing therein data by subtracting the amount of stored data from the total capacity of the memory 183 of the DAS 18 for storing therein the scan data. By calculating the residual capacity before the scan indicated by the scan plan is performed, the available capacity calculating function 45*g* can acquire information about the residual capacity of the memory 41 before the scan indicated by the scan plan is performed.

The available capacity notification function 45*h* acquires the information about the residual capacity of the memory 183 of the DAS 18 before the scan indicated by the scan plan is performed. The available capacity notification function 45*h* then issues a notification of the information about the residual capacity of the memory 183. The available capacity notification function 45*h* is an example of an acquisition unit and a notification unit.

For example, the available capacity notification function 45*h* issues a notification of the information about the residual capacity of the memory 183 based on a calculation result of the scan plan and the transfer timing for each piece of the scan data. More specifically, the available capacity notification function 45*h* acquires the calculation result calculated by the available capacity calculating function 45*g*. Due to this, the available capacity notification function 45*h* issues a notification of the information about the residual capacity of the memory 183.

The available capacity notification function 45*h* may acquire the information about the residual capacity of the memory 183 not only by calculation but also by using a monitoring result of the memory 183. For example, the available capacity notification function 45*h* issues a notification of the information about the residual capacity of the memory 183 based on the monitoring result acquired by the available capacity monitoring function 184*e* (refer to FIG. 3) of the DAS 18. More specifically, the available capacity notification function 45*h* acquires the information about the residual capacity of the memory 183 from the available capacity monitoring function 184*e* of the DAS 18. The available capacity notification function 45*h* then issues a notification of the acquired information about the residual capacity of the memory 183.

Under the condition that the residual capacity of the memory 183 of the DAS 18 becomes insufficient in a case in which the scan indicated by the scan plan is performed, the alternative plan output function 45*i* outputs an alternative plan for the scan plan to cause the data amount to be able to be stored in the memory 183. The alternative plan output function 45*i* is an example of an output unit. That is, the alternative plan output function 45*i* outputs the alternative plan for the scan plan in a case in which the available capacity notification function 45*h* determines that the available capacity of the memory 183 is insufficient.

For example, the alternative plan output function 45*i* outputs the alternative plan for reducing the data amount acquired by the scan indicated by the scan plan. Specifically, the alternative plan output function 45*i* outputs the alternative plan obtained by changing settings such as a slice thickness, a scanning range in the body axis direction, a view rate indicating a rate of a projection position per a rotation of the X-ray detector 12, and a field of view (FOV) indicating a scanning range in a channel direction. These settings are merely examples, and the alternative plan output function 45*i* may output an alternative plan obtained by changing other settings. For example, the X-ray CT apparatus 1 is a photon counting (PC) type, the alternative plan output function 45*i* may output an alternative plan obtained by changing the number of energy bins. Due to this, the data amount acquired by the DAS 18 is reduced, so that the alternative plan output function 45*i* can prevent the available capacity of the memory 183 of the DAS 18 from being insufficient.

Alternatively, the alternative plan output function 45*i* outputs an alternative plan for prolonging a time interval between scans indicated by the scan plan. Due to this, the DAS 18 is enabled to transfer a larger amount of scan data to the console 40 by the time when the next scan is performed. Accordingly, the alternative plan output function 45*i* can prevent the available capacity of the memory 183 of the DAS 18 from being insufficient.

Furthermore, the alternative plan output function 45*i* may output an alternative plan for reducing the data amount acquired by the scan, and prolonging the time interval between the scans. By prolonging the time interval between the scans, the X-ray CT apparatus 1 can perform the next scan after transferring a larger amount of scan data. Accordingly, the X-ray CT apparatus 1 can perform the scan without causing an overflow even when the available capacity of the memory 183 is small. An output method of the alternative plan output function 45*i* is not limited. For example, the alternative plan output function 45*i* may cause the display 42 of the console 40 to display the alternative plan to be output, may output the alternative plan by voice and the like, may output the alternative plan by printing, or may transmit the alternative plan to an information processing apparatus connected via a network to be output.

The storage propriety notification function 45*j* issues a notification that the data amount that can be stored in the memory 183 of the DAS 18 is exceeded in a case in which the scan indicated by the scan plan is performed. The storage propriety notification function 45*j* is an example of a notification unit. More specifically, the storage propriety notification function 45*j* determines whether the data amount that can be stored in the memory 183 is exceeded based on the data amount of the scan data that is acquired in a case in which the scan indicated by the scan plan is performed, and the information about the residual capacity of the memory 183 acquired by the available capacity notification function 45*h*. In a case in which the data amount that can be stored in the memory 183 is exceeded, the storage propriety notification function 45*j* issues a notification that the data amount that can be stored in the memory 183 is exceeded. A notification method of the storage propriety notification function 45*j* is not limited. For example, the storage propriety notification function 45*j* may cause the display 42 of the console 40 to display a notification, may make a notification by voice and the like, or may make a notification by transmitting the notification to an information processing apparatus connected via a network.

The transfer time notification function 45*k* issues a notification of a transfer time of the scan data based on the data amount that is acquired in a case in which the scan indicated by the scan plan is performed, and the transfer speed of the data from the memory 183 of the DAS 18 to the memory 41 of the console 40. The transfer time notification function 45*k* is an example of a time notification unit. The transfer speed of the data is determined based on specifications of an interface of the DAS 18, a communication line connecting the DAS 18 with the console 40, an interface of the console 40, and the like. The transfer time notification function 45*k* calculates the transfer time by multiplying the data amount of the scan data that is acquired in a case in which the scan indicated by the scan plan is performed by the transfer speed. Due to this, the transfer time notification function 45*k* issues a notification of the transfer time of the scan data that is acquired in a case in which the scan indicated by the scan plan is performed.

Furthermore, the transfer time notification function 45*k* may issue a notification of a remaining time until the transfer is completed by subtracting an elapsed time after starting the transfer from the calculated transfer time. A notification method of the transfer time notification function 45*k* is not limited. For example, the transfer time notification function 45*k* may cause the display 42 of the console 40 to display a notification, may make a notification by voice and the like, or may make a notification by transmitting the notification to an information processing apparatus connected via a network.

The data specifying function 45*l* specifies where the data stored in the memory 41 belongs to. In other words, the data specifying function 45*l* specifies the scan by which the scan data stored in the memory 41 is acquired. The data specifying function 45*l* is an example of a specification unit. More specifically, the data specifying function 45*l* specifies the scan by which the data transferred from the memory 183 of the DAS 18 is acquired based on a first identifier given to each scan in the scan plan constituted of a plurality of scans. The first identifier is identification information for identifying the scan data. That is, the data specifying function 45*l* specifies the scan by which the scan data is acquired based on the first identifier associated with the scan data.

The data specifying function 45*l* also specifies the scan plan including the scan by which the data transferred from the memory 183 of the DAS 18 is acquired based on a second identifier. The second identifier is identification information for identifying the scan plan. That is, the data specifying function 45*l* specifies the scan plan including the scan by which the scan data is acquired based on the second identifier associated with the scan data. Due to this, the reconstruction processing function 45*c* can specify the scan data acquired by the same scan plan, and can specify the order in which the scan data in the scan plan is acquired.

Next, the following describes details about the DAS 18. FIG. 3 is a block diagram illustrating an example of a configuration of the DAS 18 according to the first embodiment.

The DAS 18 includes an amplifier 181, an A/D converter 182, the memory 183, and a processing circuitry 184.

The amplifier 181 performs amplification processing on electric signals output from the respective X-ray detection elements of the X-ray detector 12. Due to this, the amplifier 181 amplifies the electric signals.

The A/D converter 182 converts the electric signal amplified by the amplifier 181 into a digital signal. For example, the A/D converter 182 performs A/D conversion processing on the electric signal output from each of the X-ray detection elements of the X-ray detector 12 to acquire detection data. The A/D converter 182 then causes the memory 183 to store therein the acquired detection data.

The memory 183 is, for example, implemented by a semiconductor memory element such as a RAM and a flash memory, a hard disk, an optical disc, and the like. The memory 183 stores therein the detection data. That is, the memory 183 temporarily stores therein the data detected by the X-ray detector 12. The memory 183 is an example of a buffer.

The processing circuitry 184 controls an operation of the entire DAS 18. The processing circuitry 184 has, for example, a plan acquisition function 184*a*, a giving function 184*b*, a transfer timing determining function 184*c*, a transfer function 184*d*, and the available capacity monitoring function 184*e*. In the embodiment, respective processing functions performed by the plan acquisition function 184*a*, the giving function 184*b*, the transfer timing determining function 184*c*, the transfer function 184*d*, and the available capacity monitoring function 184*e* as constituent elements are stored in the memory 183 in a form of a computer-executable program. The processing circuitry 184 is a processor that implements a function corresponding to each computer program by reading out the computer program from the memory 183 to be executed. In other words, the processing circuitry 184 that has read out each computer program is assumed to have each function indicated in the processing circuitry 184 in FIG. 3.

Regarding FIG. 3, it is assumed that a single processor implements the plan acquisition function 184a, the giving function 184b, the transfer timing determining function 184c, the transfer function 184d, and the available capacity monitoring function 184e. Alternatively, the processing circuitry 184 may be configured by combining a plurality of independent processors, and each of the processors may execute the computer program to implement the function. Regarding FIG. 3, it is assumed that a single storage circuit such as the memory 183 stores therein the computer program corresponding to each of the processing functions. Alternatively, a plurality of storage circuits may be arranged in a distributed manner, and the processing circuitry 184 may be configured to read out a corresponding computer program from an individual storage circuit.

A word of "processor" used in the above description means, for example, a CPU, a GPU, or a circuit such as an application specific integrated circuit, a programmable logic device, a complex programmable logic device, and a field programmable gate array. The processor implements the function by reading out and executing the computer program stored in the memory 183. The configuration may be made such that the computer program is directly incorporated in a circuit of the processor instead of being stored in the memory 183. In this case, the processor implements the function by reading out and executing the computer program incorporated in the circuit.

The plan acquisition function 184a acquires instructions for a scan and transfer from the console 40. For example, the plan acquisition function 184a acquires the scan plan and the transfer plan. Due to this, the plan acquisition function 184a acquires a series of instructions indicated by the scan plan and the transfer plan.

Alternatively, the plan acquisition function 184a may acquire the instructions indicated by the scan plan and the transfer plan as occasion demands. For example, the plan acquisition function 184a acquires information indicating the first identifier and the second identifier that indicate a transfer target in a case in which the trigger indicated by the transfer plan is generated. Due to this, the plan acquisition function 184a can specify a transfer timing and the transfer target.

The plan acquisition function 184a also acquires a notification indicating suspension of transfer from the console 40. Due to this, the plan acquisition function 184a grasps that an interrupt of the scan plan occurs.

The giving function 184b gives the first identifier for identifying the scan to the scan data acquired by each scan in the scan plan. Additionally, the giving function 184b gives the second identifier for identifying the scan plan to the scan data acquired by each scan in the scan plan. The giving function 184b is an example of a giving unit. More specifically, the giving function 184b gives the first identifier to each piece of the scan data based on the scan plan acquired by the plan acquisition function 184a. For example, the giving function 184b gives the order of scans in the scan plan as the first identifier. As the first identifier, other information may be given other than the order of scans. In this way, by giving the first identifier, the console 40 can identify the scan by which the scan data is acquired without transmitting the scan data in the order indicated by the scan plan.

Similarly, the giving function 184b gives the second identifier to each piece of the scan data based on the scan plan acquired by the plan acquisition function 184a. For example, the giving function 184b gives, as the second identifier, information such as identification information for identifying the subject P as a target of the scan plan, or identification information for identifying an examination executed by the scan plan. That is, the giving function 184b gives the first identifier and the second identifier to each piece of the scan data. In this way, by giving the first identifier and the second identifier, the console 40 can identify the scan plan of the scan data without transmitting the scan data in the order indicated by the scan plan.

The transfer timing determining function 184c controls transfer of the scan data in units of a scan, the scan data acquired by each scan of the scan plan constituted of a plurality of scans. More specifically, the transfer timing determining function 184c determines the transfer timing of the scan data from the memory 183 of the DAS 18 to the memory 41 of the console 40 based on the scan plan and the information about the residual capacity of the memory 183. The transfer timing determining function 184c is an example of a determination unit. That is, the transfer timing determining function 184c determines the transfer timing for transferring the scan data from the memory 183 to the memory 41 of the console 40 for operating the X-ray CT apparatus 1. The planning function 45d generates the transfer plan based on the scan plan, the information about the residual capacity of the memory 183, and the transfer speed of the scan data from the memory 183 of the DAS 18 to the memory 41 of the console 40. The transfer timing determining function 184c determines the transfer timing based on the transfer plan generated by the planning function 45d. That is, the transfer timing determining function 184c determines to transfer the scan data at the transfer timing indicated by the transfer plan.

Alternatively, the transfer timing determining function 184c acquires a transfer request from the console 40 each time the scan data is transferred. The transfer timing determining function 184c then causes a timing specified by the transfer request to be the transfer timing of the scan data. Due to this, the transfer timing determining function 184c determines the transfer timing of the scan data.

In a case in which an interrupt of the scan plan is instructed, the transfer timing determining function 184c determines to resume transfer after the data acquired by the scan plan is transferred. Due to this, the transfer timing determining function 184c causes the scan data as the interruption target to be transferred with priority.

The transfer function 184d transfers the scan data at the transfer timing determined by the transfer timing determining function 184c. More specifically, the transfer function 184d causes the transmitter 21 to transmit the first identifier, the second identifier, and the scan data in association with each other.

The plan acquisition function 184a may be instructed to suspend transfer of the scan data by the console 40 in a case in which an interrupt of the scan plan is designated. In a case of receiving a notification for suspending transfer of the scan data, the transfer function 184d notifies the console 40 of the first identifier and the second identifier indicating the scan data that has been completely transferred. Due to this, the console 40 can specify the scan data from which the transfer should be resumed. For example, in a case in which there is the possibility that the transfer function 184d suspend transfer in the middle of transferring the scan data, the console 40 cannot determine whether transfer is suspended in the middle of transferring the scan data, or all pieces of the scan data have been transferred. Even in such a case, by issuing a notification of the scan data that has been completely transferred, the console 40 can specify the scan data from which transfer should be resumed.

The available capacity monitoring function 184e monitors the available capacity of the memory 183. More specifically, the available capacity monitoring function 184e monitors the data amount written into the memory 183, and the data amount read out from the memory 183. Due to this, the available capacity monitoring function 184e measures the available capacity of a storage region of the memory 183 in which the scan data can be stored. The available capacity monitoring function 184e then notifies the console 40 of a measurement result as the information about the residual capacity of the memory 183.

Figure 4:
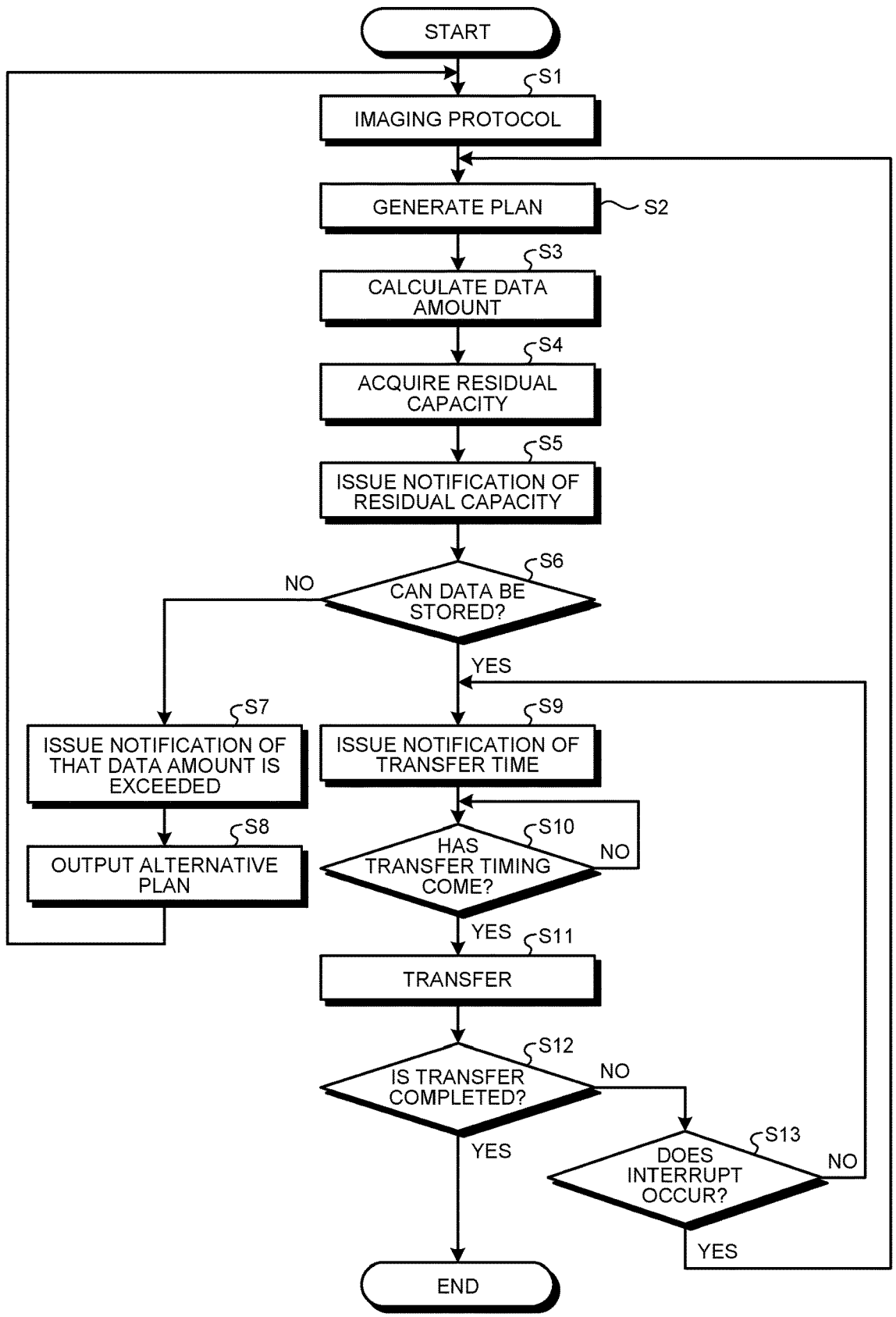
FIG. 4 is a flowchart illustrating an example of first transfer processing performed by the X-ray CT apparatus according to the first embodiment.

Next, the following describes first transfer processing performed by the X-ray CT apparatus 1. The first transfer processing is processing of transferring the scan data so that the memory 183 does not overflow. FIG. 4 is a flowchart illustrating an example of the first transfer processing performed by the X-ray CT apparatus 1 according to the first embodiment.

The operation control function 45a receives an input of the imaging protocol (Step S1).

The planning function 45d generates the scan plan and the transfer plan based on the received imaging protocol (Step S2).

The available capacity calculating function 45g calculates the data amount of the scan data that is acquired by the generated scan plan (Step S3).

The available capacity notification function 45h acquires the information about the residual capacity of the memory 183 of the DAS 18 from the available capacity calculating function 45g (Step S4). Alternatively, the available capacity notification function 45h acquires the information about the residual capacity of the memory 183 from the available capacity monitoring function 184e.

The available capacity notification function 45h issues a notification of the residual capacity of the memory 183 based on the information about the residual capacity of the memory 183 (Step S5). The available capacity notification function 45h may also issue a notification of the residual capacity of the memory 183 at another step other than Step S5.

The storage propriety notification function 45j determines whether the scan data can be stored in the memory 183 based on the information about the residual capacity of the memory 183 and the data amount of the scan data acquired by the scan plan (Step S6). That is, the storage propriety notification function 45j determines whether the available capacity of the memory 183 is insufficient.

In a case in which the scan data cannot be stored due to insufficiency of the available capacity of the memory 183 (No at Step S6), the storage propriety notification function 45j issues a notification that the data amount that can be stored in the memory 183 is exceeded in a case in which the scan indicated by the scan plan is performed (Step S7).

The alternative plan output function 45i outputs an alternative plan for the scan plan to enable the data amount to be stored by the memory 183 (Step S8). The operation control function 45a then returns the process to Step S1, and receives an input of the imaging protocol indicated by the alternative plan.

In a case in which the scan data can be stored in the memory 183 (Yes at Step S6), the transfer time notification function 45k issues a notification of the transfer time of the scan data based on the data amount of the scan data, and the transfer speed of the scan data from the memory 183 of the DAS 18 to the memory 41 of the console 40 (Step S9).

The transfer function 184d determines whether the transfer timing for transferring the scan data scanned by the scan plan comes (Step S10). That is, the transfer function 184d determines whether the transfer request for the scan data is received.

In a case in which the transfer timing has not come (No at Step S10), the transfer function 184d stands by for transfer of the scan data. In a case in which the transfer timing comes (Yes at Step S10), the transfer function 184d transfers the scan data, the first identifier, and the second identifier in association with each other (Step S11).

The transfer function 184d determines whether the transfer indicated by the transfer plan is completed (Step S12).

In a case in which the transfer of the scan data is not completed (No at Step S12), the operation control function 45a determines whether an instruction for an interrupt of the scan plan is made (Step S13). That is, the operation control function 45a determines whether the imaging protocol making an instruction for an interrupt of the scan plan is input.

In a case in which the instruction for an interrupt of the scan plan is not made (No at Step S13), the X-ray CT apparatus 1 returns the process to Step S9, and continuously gives the first identifier and the second identifier to the scan data, and transfers the scan data.

In a case in which the instruction for an interrupt of the scan plan is made (Yes at Step S13), the planning function 45d returns the process to Step S2, and generates the scan plan and the transfer plan including the imaging protocol of the interruption target. Due to this, the X-ray CT apparatus 1 performs remaining pieces of processing after executing the instructed interrupt.

At Step S5, in a case in which the transfer of the scan data ends (Yes at Step S12), the X-ray CT apparatus 1 ends the first transfer processing.

As described above, the X-ray CT apparatus 1 according to the first embodiment includes the memory 183 that temporarily stores therein the data detected by the X-ray detector 12. The available capacity notification function 45h of the console 40 acquires the information about the residual capacity of the memory 183 of the DAS 18 before the scan indicated by the scan plan is performed. The transfer timing determining function 184c determines the transfer timing of the scan data based on the transfer plan that is generated based on the scan plan and the information about the residual capacity of the memory 183. In this way, the X-ray CT apparatus 1 determines the transfer timing of the scan data based on the scan plan and the available capacity of the memory 183. In other words, the X-ray CT apparatus 1 transfers the scan data before the buffer overflows in accordance with subsequent scan plans. That is, the X-ray CT apparatus 1 can transfer the scan data without causing an overflow even when the X-ray CT apparatus 1 does not include a buffer having maximum capacity that can be assumed. Accordingly, the X-ray CT apparatus 1 can scan the subject P while preventing the storage capacity of the buffer from being increased.

Second Embodiment

In the description about the X-ray CT apparatus 1 according to the first embodiment, the DAS 18 includes the buffer that temporarily stores therein the scan data detected by the X-ray detector 12. In an X-ray CT apparatus 1a according to a second embodiment, the buffer is included in a relay circuitry 50 instead of a DAS 18a.

Figure 5:
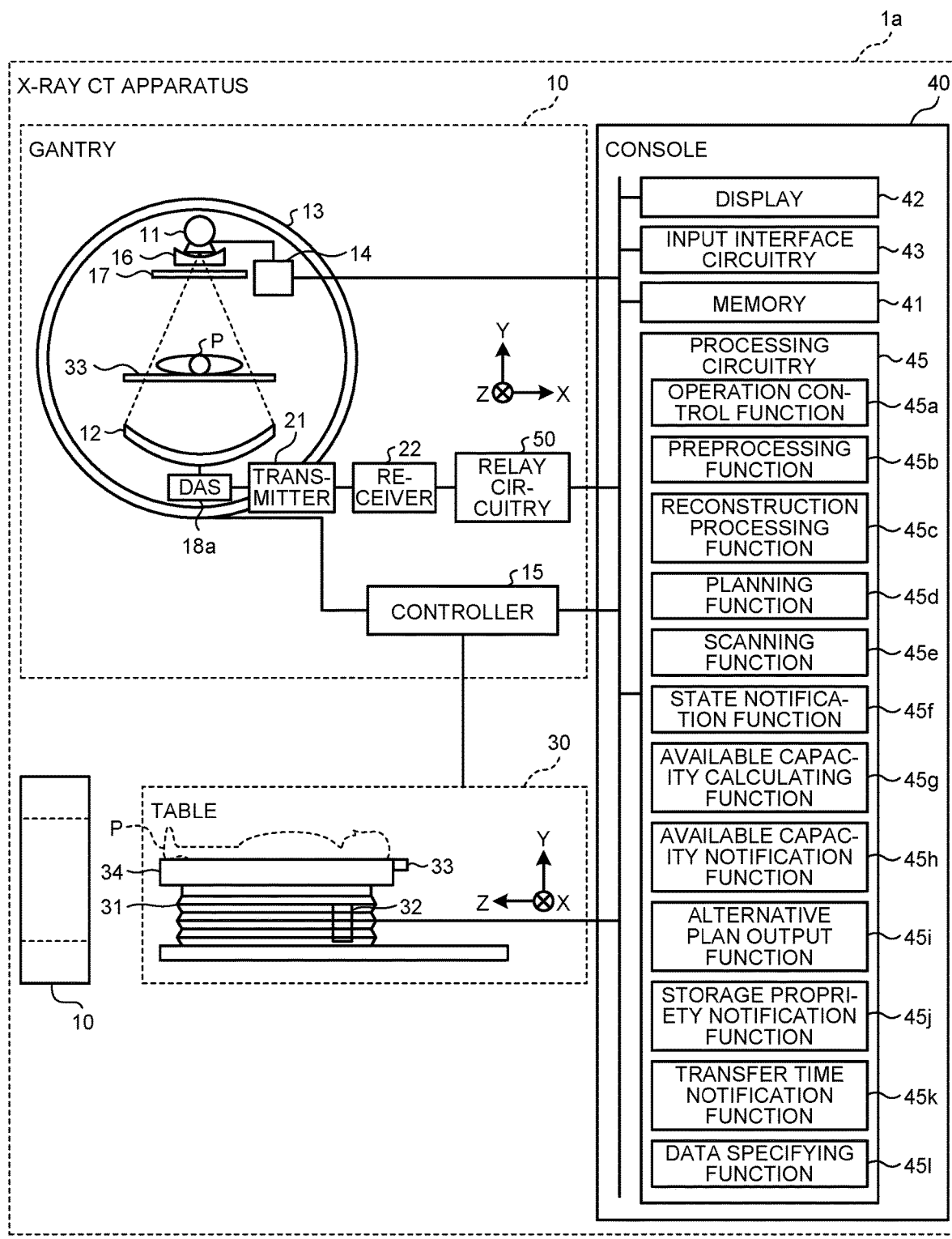
FIG. 5 is a block diagram illustrating an example of a configuration of an X-ray CT apparatus according to a second embodiment.

FIG. 5 is a block diagram illustrating an example of a configuration of the X-ray CT apparatus 1a according to the second embodiment. The relay circuitry 50 is arranged to be closer to the console 40 side than the receiver 22 that is arranged on the non-rotation portion of the gantry 10 such as the fixed frame. Due to this, the X-ray CT apparatus 1a can efficiently transfer the data even in a case in which the transfer speed on the console 40 side is slower than that of the receiver 22.

Figure 6:
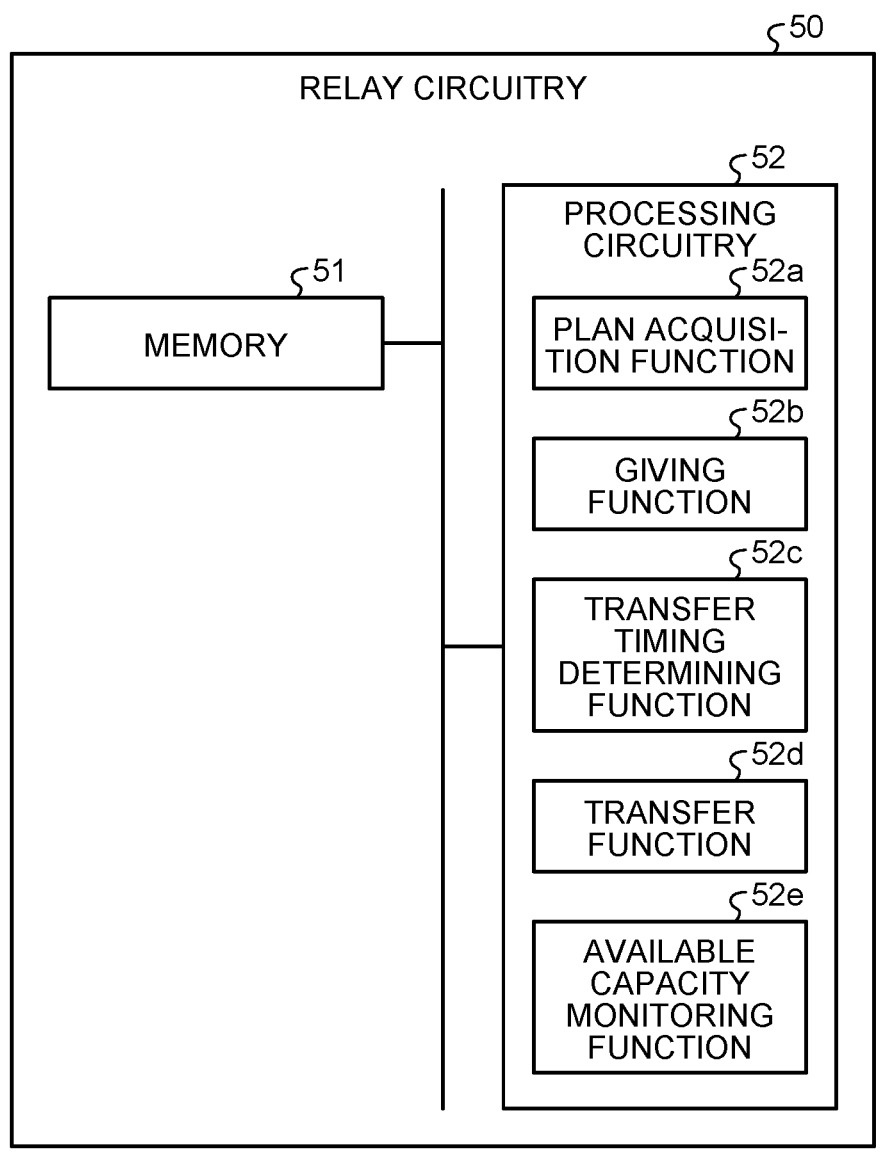
FIG. 6 is a block diagram illustrating an example of a configuration of a relay circuitry according to the second embodiment.

Next, the following describes details about the relay circuitry 50. FIG. 6 is a block diagram illustrating an example of a configuration of the relay circuitry 50 according to the second embodiment.

The relay circuitry 50 includes a memory 51 and a processing circuitry 52.

The memory 51 is, for example, implemented by a semiconductor memory element such as a RAM and a flash memory, a hard disk, an optical disc, and the like. The memory 51 stores therein the detection data. That is, the memory 51 temporarily stores therein the data detected by the X-ray detector 12.

The processing circuitry 52 controls an operation of the entire relay circuitry 50. Regarding the processing circuitry 52, for example, respective processing functions performed by a plan acquisition function 52a, a giving function 52b, a transfer timing determining function 52c, a transfer function 52d, and an available capacity monitoring function 52e are stored in the memory 51 in a form of a computer-executable program. The processing circuitry 52 is a processor that implements a function corresponding to each computer program by reading out the computer program from the memory 51 to be executed. In other words, the processing circuitry 52 that has read out each computer program is assumed to have each function indicated in the processing circuitry 52 in FIG. 6.

Regarding FIG. 6, it is assumed that a single processor implements the plan acquisition function 52a, the giving function 52b, the transfer timing determining function 52c, the transfer function 52d, and the available capacity monitoring function 52e. Alternatively, the processing circuitry 52 may be configured by combining a plurality of independent processors, and each of the processors may execute the computer program to implement the function. Regarding FIG. 6, it is assumed that a single storage circuit such as the memory 51 stores therein the computer program corresponding to each of the processing functions. Alternatively, a plurality of storage circuits may be arranged in a distributed manner, and the processing circuitry 52 may be configured to read out a corresponding computer program from an individual storage circuit.

A word of "processor" used in the above description means, for example, a CPU, a GPU, or a circuit such as an application specific integrated circuit, a programmable logic device, a complex programmable logic device, and a field programmable gate array. The processor implements the function by reading out and executing the computer program stored in the memory 51. The configuration may be made such that the computer program is directly incorporated in a circuit of the processor instead of being stored in the memory 51. In this case, the processor implements the function by reading out and executing the computer program incorporated in the circuit.

The plan acquisition function 52a has a function similar to the plan acquisition function 184a of the DAS 18.

The giving function 52b has a function similar to the giving function 184b of the DAS 18.

The transfer timing determining function 52c has a function similar to the transfer timing determining function 184c of the DAS 18. That is, the transfer timing determining function 52c determines a transfer timing for transferring data from the memory 183 to the memory 51 of the relay circuitry 50 that relays communication between the memory 183 and the console 40.

The transfer function 52d has a function similar to the transfer function 184d of the DAS 18.

The available capacity monitoring function 52e has a function similar to the available capacity monitoring function 184e of the DAS 18.

As described above, the X-ray CT apparatus 1a according to the second embodiment includes the memory 51 that temporarily stores therein the data detected by the X-ray detector 12. The available capacity notification function 45h of the console 40 acquires information about residual capacity of the memory 51 of the relay circuitry 50 before the scan indicated by the scan plan is performed. The transfer timing determining function 184c determines the transfer timing of the scan data based on the transfer plan that is generated based on the scan plan and the information about the residual capacity of the memory 51. In other words, the X-ray CT apparatus 1a transfers the scan data before the buffer overflows in accordance with subsequent scan plans. Accordingly, the X-ray CT apparatus 1a can scan the subject P while preventing the storage capacity of the buffer from being increased.

First Modification

The second embodiment describes a case in which the relay circuitry 50, instead of the DAS 18, includes the buffer that temporarily stores therein the scan data detected by the X-ray detector 12. The buffer that temporarily stores therein the scan data detected by the X-ray detector 12 may be arranged on both of the DAS 18 and the relay circuitry 50.

For example, in a case in which the transfer speed of the X-ray detector 12 and the following units is slower than an acquisition speed of the scan data, an X-ray CT apparatus 1b can efficiently transfer the scan data by arranging the buffer on the DAS 18. Furthermore, in a case in which the transfer speed from the receiver 22 to the console 40 is slower than the transfer speed from the DAS 18 to the receiver 22, the X-ray CT apparatus 1b can efficiently transfer the scan data by arranging the buffer on the DAS 18.

Second Modification

In the description about the embodiment described above, the DAS 18 transfers the scan data to the console 40 when the scan data is not acquired. However, the DAS 18 may transfer the scan data to the console 40 when the scan data is acquired.

Third Embodiment

The X-ray CT apparatus 1 transfers the data generated by the scan while scanning the subject P. Due to this, the X-ray CT apparatus 1 can transfer the generated data with a buffer having small storage capacity without lowering a generation rate.

However, to acquire the data by repeatedly performing the scan of the subject P and transfer of the data, the user such as a health professional or the subject P needs to wait for a long time until the data is completely transferred because the data amount is large. Thus, there is a demand for a technique for reducing the waiting time of the user of the X-ray CT apparatus 1 by efficiently transferring the data.

Figure 7:
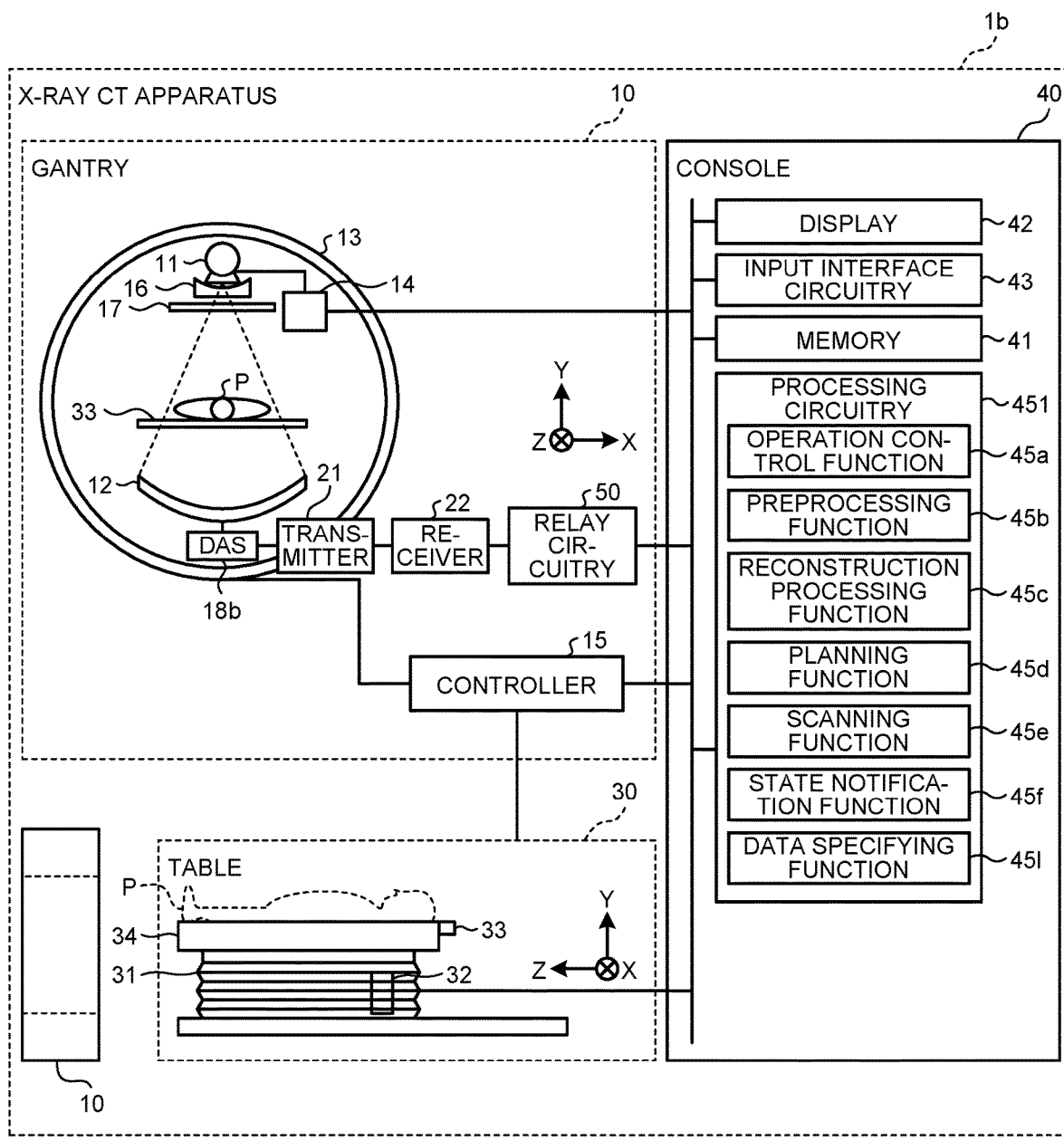
FIG. 7 is a block diagram illustrating an example of a configuration of an X-ray CT apparatus according to a third embodiment.

FIG. 7 is a block diagram illustrating an example of a configuration of the X-ray CT apparatus 1b according to a third embodiment.

A processing circuitry 45l of the X-ray CT apparatus 1b has the operation control function 45a, the preprocessing function 45b, the reconstruction processing function 45c, the planning function 45d, the scanning function 45e, the state notification function 45f, and the data specifying function 45l. That is, the processing circuitry 45l does not have the available capacity calculating function 45g, the available capacity notification function 45h, the alternative plan output function 45i, the storage propriety notification function 45j, and the transfer time notification function 45k.

The operation control function 45a has substantially the same function as the operation control function 45a according to the first embodiment.

The preprocessing function 45b has substantially the same function as the preprocessing function 45b according to the first embodiment.

The reconstruction processing function 45c has substantially the same function as the reconstruction processing function 45c according to the first embodiment.

The planning function 45d has substantially the same function as the planning function 45d according to the first embodiment.

The scanning function 45e has substantially the same function as the scanning function 45e according to the first embodiment.

The state notification function 45f has substantially the same function as the state notification function 45f according to the first embodiment.

The data specifying function 45l has substantially the same function as the data specifying function 45l according to the first embodiment.

Figure 8:
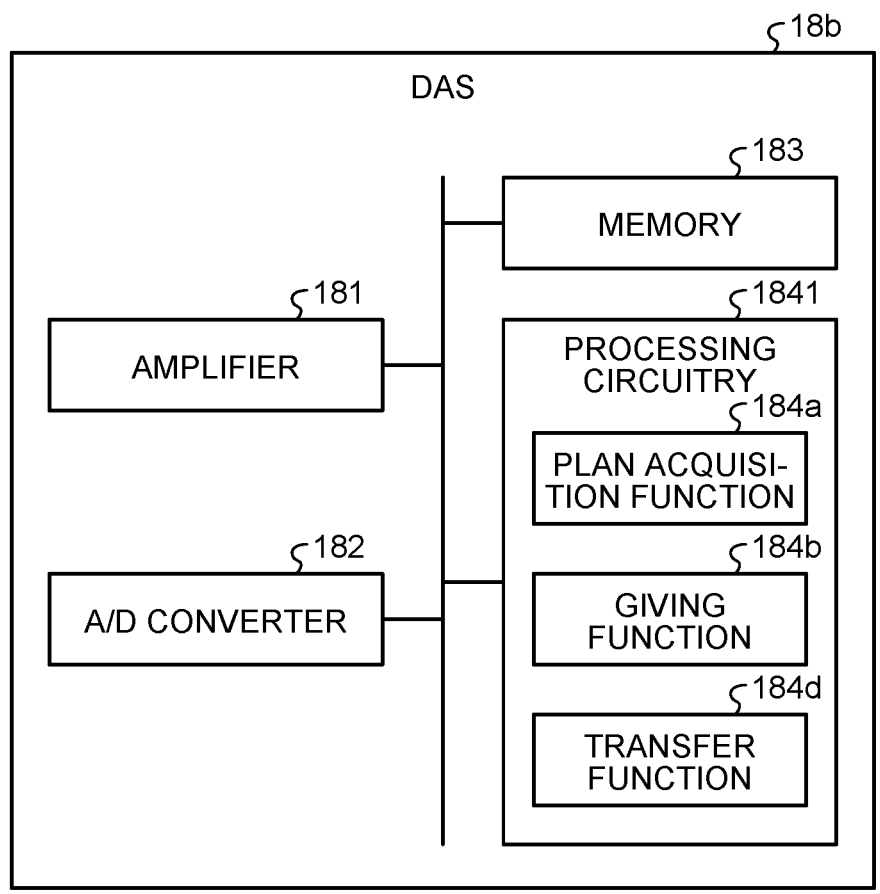
FIG. 8 is a block diagram illustrating an example of a configuration of a DAS according to the third embodiment.

Next, the following describes details about a DAS 18b according to the third embodiment. FIG. 8 is a block diagram illustrating an example of a configuration of the DAS 18b according to the third embodiment.

A processing circuitry 1841 of the DAS 18b has the plan acquisition function 184a, the giving function 184b, and the transfer function 184d. That is, the processing circuitry 1841 does not have the transfer timing determining function 184c and the available capacity monitoring function 184e.

The plan acquisition function 184a has substantially the same function as the plan acquisition function 184a according to the first embodiment.

The giving function 184b has substantially the same function as the giving function 184b according to the first embodiment.

The transfer function 184d has substantially the same function as the transfer function 184d according to the first embodiment. That is, the transfer function 184d causes the detection data to be transferred based on the transfer plan. The transfer function 184d is an example of a transfer unit. More specifically, the transfer function 184d specifies an address in the memory 183 at which the scan data designated by the transfer plan is stored. The transfer function 184d then causes the transmitter 21 to transfer the scan data at the specified address. In this way, the transfer function 184d causes the transmitter 21 to transmit the detection data stored in the memory 183.

The first identifier is given to the scan data by the giving function 184b. Thus, the transfer function 184d transfers the scan data and the first identifier in association with each other based on the transfer plan indicating the order of transferring the scan data acquired by the scan. To efficiently transfer the scan data, the transfer plan may include an instruction to transfer the scan data in an order different from the order of scans indicated by the scan plan in some cases. In this case, the transfer function 184d transfers the scan data in an order different from the order of scans based on the transfer plan.

The first identifier and the second identifier are given to the scan data by the giving function 184b. The transfer function 184d transfers the scan data, the first identifier, and the second identifier in association with each other. To efficiently transfer the scan data, the transfer plan may include an instruction to transfer the scan data in an order different from the order of the scan plan indicated by the scan plan in some cases. The transfer function 184d transfers the data in an order different from the order of the scan plan.

The scan plan indicates that, in a case in which an interrupt of the scan plan is designated, the scan data of the scan plan as an interruption target is transferred earlier. In a case in which an interrupt of the scan plan occurs after the order of transferring the scan data is determined based on the scan plan, the transfer function 184d causes the scan data of the scan plan as the interruption target to be transferred earlier.

Figure 9:
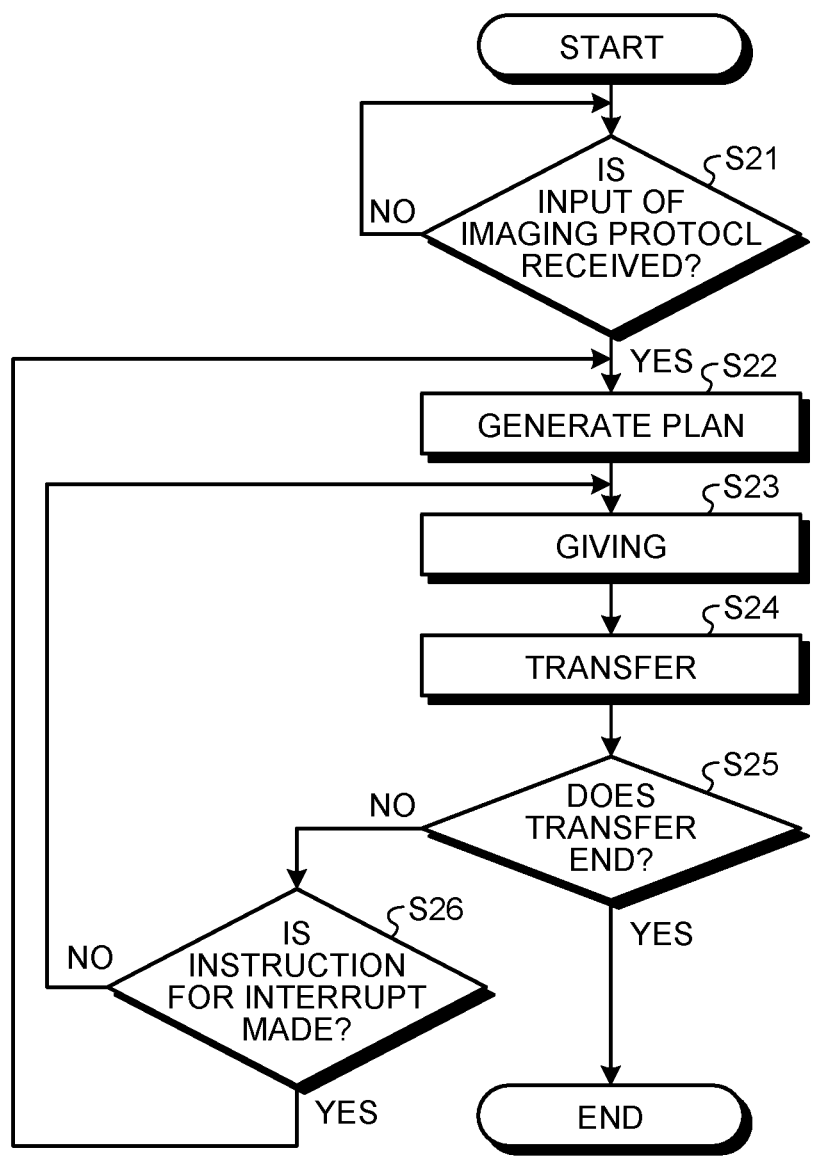
FIG. 9 is a flowchart illustrating an example of second transfer processing performed by the X-ray CT apparatus according to the third embodiment.

Next, the following describes second transfer processing performed by the X-ray CT apparatus 1b according to the third embodiment. In the first transfer processing, the scan data is transferred so that the memory 183 does not overflow. On the other hand, the second transfer processing is processing of transferring the scan data while giving the first identifier and the second identifier thereto. FIG. 9 is a flowchart illustrating an example of the second transfer processing performed by the X-ray CT apparatus 1b according to the third embodiment.

The operation control function 45a determines whether an input of the imaging protocol is received (Step S21). In a case in which the input of the imaging protocol is not received (No at Step S21), the operation control function 45a stands by until the imaging protocol is input.

In a case in which the input of the imaging protocol is received (Yes at Step S21), the planning function 45d generates the scan plan and the transfer plan based on the received imaging protocol (Step S22).

The giving function 184b gives the first identifier and the second identifier to the scan data that is acquired based on the scan plan and designated by the transfer plan (Step S23).

The transfer function 184d transfers the scan data designated by the transfer plan, and the given first identifier and second identifier in association with each other (Step S24).

The transfer function 184d determines whether transfer of the scan data designated by the transfer plan ends (Step S25). In a case in which the transfer of the scan data has not ended (No at Step S25), the operation control function 45a determines whether an instruction for an interrupt of the scan plan is made (Step S26). That is, the operation control function 45a determines whether the imaging protocol making an instruction for an interrupt of the scan plan is input.

In a case in which the instruction for an interrupt of the scan plan is not made (No at Step S26), the X-ray CT apparatus 1b returns the process to Step S23, and continuously gives the first identifier and the second identifier to the scan data, and transfers the scan data.

In a case in which the instruction for an interrupt of the scan plan is made (Yes at Step S26), the planning function 45d returns the process to Step S23, and generates the scan plan and the transfer plan including the imaging protocol of the interruption target. Due to this, the X-ray CT apparatus 1b performs remaining pieces of processing after executing the instructed interrupt.

As described above, the DAS 18b according to the third embodiment includes the memory 183 that temporarily stores therein the scan data detected by the X-ray detector 12. The console 40 specifies the scan by which the scan data transferred from the memory 183 is acquired based on the first identifier given to each scan in the scan plan constituted of a plurality of scans. Due to this, the console 40 can specify the scan by which the data is acquired even in a case in which the scan data is transferred from the DAS 18b in an order different from the order of scans. That is, the DAS 18b can select and transfer the scan data in accordance with not only the order of scans but also a situation of a transfer route. Accordingly, the X-ray CT apparatus 1b can reduce the waiting time of the user of the X-ray CT apparatus 1b.

Fourth Embodiment

In the description about the X-ray CT apparatus 1b according to the third embodiment, the DAS 18b includes the buffer that temporarily stores therein the scan data detected by the X-ray detector 12. In an X-ray CT apparatus 1c according to a fourth embodiment, the buffer is included in a relay circuitry 50a instead of a DAS 18c.

Figure 10:
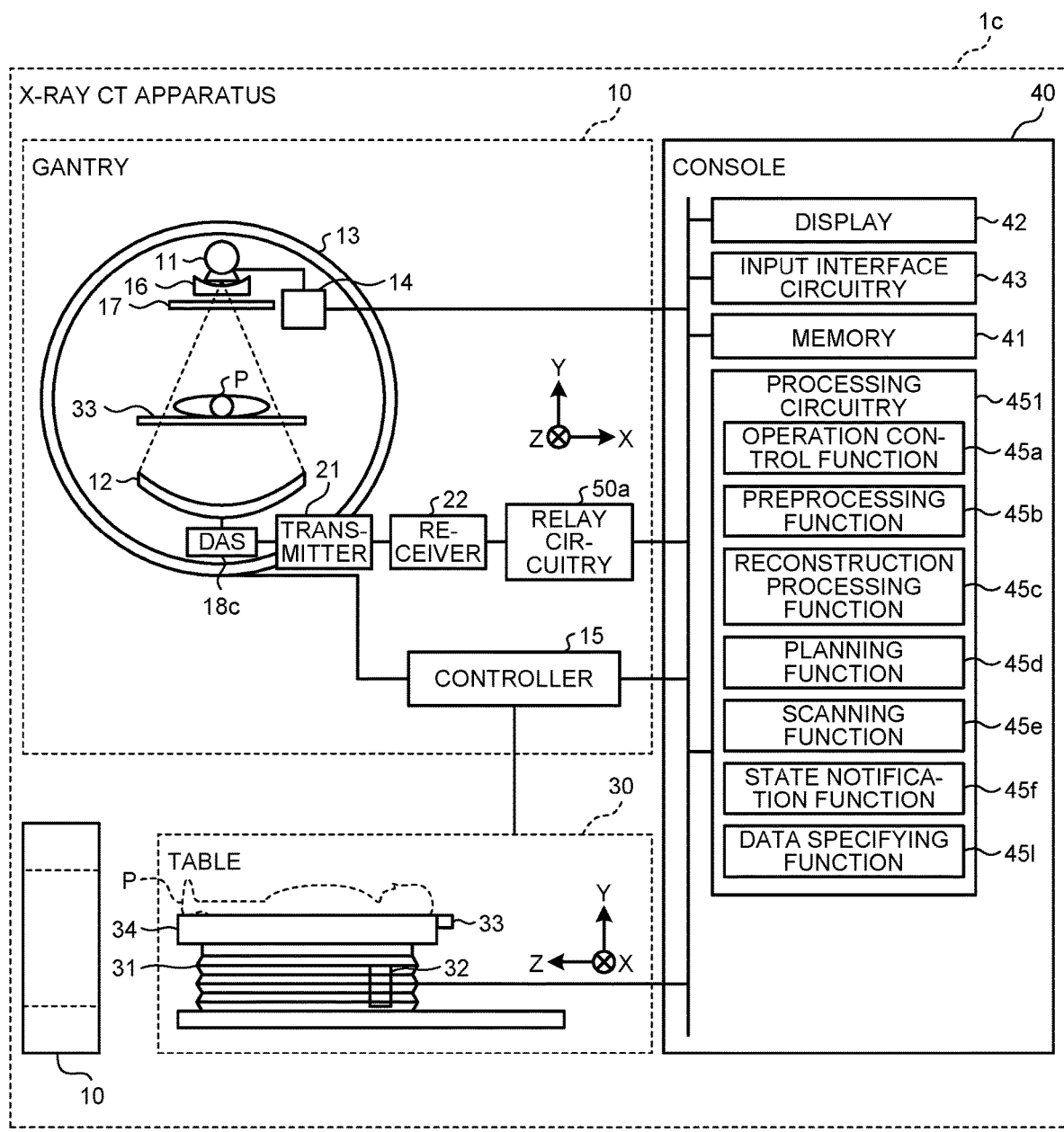
FIG. 10 is a block diagram illustrating an example of a configuration of an X-ray CT apparatus according to a fourth embodiment.

FIG. 10 is a block diagram illustrating an example of a configuration of the X-ray CT apparatus 1c according to the fourth embodiment. The relay circuitry 50a is arranged to be closer to the console 40 side than the receiver 22 arranged on the non-rotation portion of the gantry 10 such as the fixed frame. Due to this, the X-ray CT apparatus 1c can efficiently transfer the data even in a case in which the transfer speed on the console 40 side is slower than that of the receiver 22.

Figure 11:
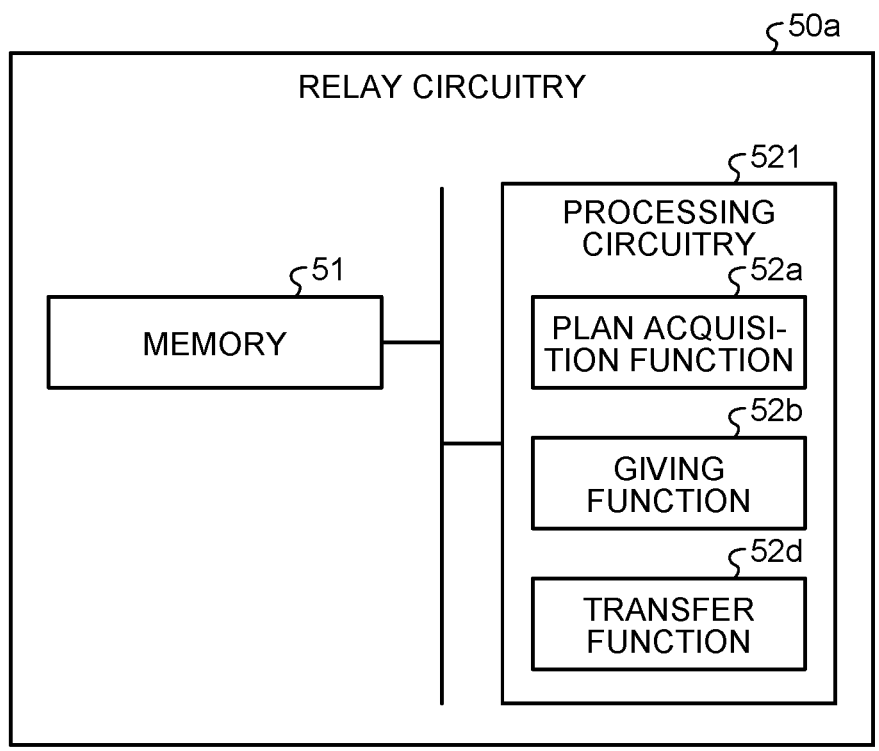
FIG. 11 is a block diagram illustrating an example of a configuration of a relay circuitry according to the fourth embodiment.

Next, the following describes details about the relay circuitry 50a. FIG. 11 is a block diagram illustrating an example of a configuration of the relay circuitry 50a according to the fourth embodiment.

A processing circuitry 521 of the relay circuitry 50a includes the plan acquisition function 52a, the giving function 52b, and the transfer function 52d. That is, the processing circuitry 521 does not have the transfer timing determining function 52c and the available capacity monitoring function 52e.

The plan acquisition function 52a has a function similar to the plan acquisition function 184a of the DAS 18b.

The giving function 52b has a function similar to the giving function 184b of the DAS 18b.

The transfer function 52d has a function similar to the transfer function 184d of the DAS 18b.

As described above, the relay circuitry 50a according to the fourth embodiment includes the memory 51 that temporarily stores therein the scan data detected by the X-ray detector 12. The console 40 specifies the scan by which the scan data transferred from the memory 51 is acquired based on the first identifier given to each scan in the scan plan constituted of a plurality of scans. Due to this, the console 40 can specify the scan by which the data is acquired even in a case in which the scan data is transferred from the relay circuitry 50a in an order different from the order of scans. That is, the relay circuitry 50a can select and transfer the scan data in accordance with not only the order of scans but also a situation of a transfer route from the relay circuitry 50a to the console 40. Accordingly, the X-ray CT apparatus 1c can reduce the waiting time of the user of the X-ray CT apparatus 1c.

First Modification

The fourth embodiment describes a case in which the relay circuitry 50a, instead of the DAS 18c, includes the buffer that temporarily stores therein the scan data detected by the X-ray detector 12. The buffer that temporarily stores therein the scan data detected by the X-ray detector 12 may be arranged on both of the DAS 18c and the relay circuitry 50a.

For example, in a case in which the transfer speed of the X-ray detector 12 and the following units is slower than an acquisition speed of the scan data, the X-ray CT apparatus 1c can efficiently transfer the scan data by arranging the buffer on the DAS 18c. Furthermore, in a case in which the transfer speed from the receiver 22 to the console 40 is slower than the transfer speed from the DAS 18c to the receiver 22, the X-ray CT apparatus 1c can efficiently transfer the scan data by arranging the buffer on the DAS 18c.

Second Modification

In the description about the embodiment described above, the DAS 18c transfers the scan data to the console 40 when the scan data is not acquired. However, the DAS 18c may transfer the scan data to the console 40 when the scan data is acquired.

Third Modification

The X-ray CT apparatuses 1, 1a, 1b, and 1c have been described above in the first embodiment, the second embodiment, the first modification of the second embodiment, the second modification of the second embodiment, the third embodiment, the fourth embodiment, the first modification of the fourth embodiment, and the second modification of the fourth embodiment. The X-ray CT apparatuses 1, 1a, 1b, and 1c may be combined or partially combined with each other.

The following notes are disclosed as an aspect and an optional characteristic of the present invention regarding the embodiments described above.

Note 1. An X-ray CT apparatus comprising:
a buffer configured to temporarily store therein data detected by an X-ray detector; and
a processing circuitry configured to
receive an input of an imaging protocol,
generate a scan plan indicating a procedure of a scan instructed by the imaging protocol, and
issue a notification that, in a case in which a scan indicated by the scan plan is performed, a data amount that is able to be stored in the buffer is exceeded.

Note 2. An X-ray CT apparatus comprising:
a buffer configured to temporarily store therein data detected by an X-ray detector; and
a processing circuitry configured to
receive an input of an imaging protocol,
generate a scan plan indicating a procedure of a scan instructed by the imaging protocol,
calculate a data amount that is acquired in a case in which a scan indicated by the scan plan is performed, and
issue a notification of a transfer time of the data based on the data amount and a transfer speed of the data from the buffer to a storage circuitry.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
a buffer configured to temporarily store therein data detected by an X-ray detector; and processing circuitry configured to determine an order of a unit-of-scan-based transferring of the stored data according to a transfer time of the data, the data being acquired by each scan of a scan plan including a plurality of scans.

2. The X-ray CT apparatus according to claim 1, wherein the processing circuitry is further configured to:
acquire information about a residual capacity of the buffer before a scan indicated by the scan plan is performed, and
determine a transfer timing of the data from the buffer to storage circuitry based on the scan plan and the acquired information about the residual capacity of the buffer.

3. The X-ray CT apparatus according to claim 2, wherein the processing circuitry is further configured to output an alternative plan for the scan plan based on the residual capacity of the buffer when the scan indicated by the scan plan is performed, and a data amount that is able to be stored in the buffer.

4. The X-ray CT apparatus according to claim 3, wherein the processing circuitry is further configured to output the alternative plan, which is for reducing a data amount acquired by the scan indicated by the scan plan.

5. The X-ray CT apparatus according to claim 3, wherein the processing circuitry is further configured to output the alternative plan, which is for prolonging a time interval between a plurality of the scans indicated by the scan plan.

6. The X-ray CT apparatus according to claim 2, wherein the processing circuitry is further configured to issue a notification of the acquired information about the residual capacity of the buffer.

7. The X-ray CT apparatus according to claim 6, wherein the processing circuitry is further configured to issue a notification of the acquired information about the residual capacity of the buffer based on a monitoring result of a first data amount written into the buffer and a second data amount read out from the buffer.

8. The X-ray CT apparatus according to claim 6, wherein the processing circuitry is further configured to issue a notification of the acquired information about the residual capacity of the buffer based on a calculation result of the scan plan and the transfer timing of each piece of the data.

9. The X-ray CT apparatus according to claim 2, wherein the processing circuitry is further configured to
generate a transfer plan indicating the transfer timing based on the scan plan, the acquired information about the residual capacity of the buffer, and a transfer speed of the data from the buffer to the storage circuitry, and
determine the transfer timing based on the generated transfer plan.

10. The X-ray CT apparatus according to claim 9, wherein the processing circuitry is further configured to generate the transfer plan for transferring the data in an order different from an order of the plurality of scans indicated by the scan plan.

11. The X-ray CT apparatus according to claim 10, wherein the processing circuitry is further configured to generate, under a condition that a data amount of data acquired by the scan plan to be executed later among a plurality of the scan plans is smaller than available capacity of the buffer, the transfer plan, which includes transferring the data of the scan plan executed earlier after transferring the data acquired by the scan plan executed later.

12. The X-ray CT apparatus according to claim 10, wherein the processing circuitry is further configured to determine, when an instruction for an interrupt of the scan plan is made, to resume transfer after transferring data acquired by the scan plan.

13. The X-ray CT apparatus according to claim 2, wherein the processing circuitry is further configured to determine the transfer timing for transferring the data from the buffer to the storage circuitry, which is in a console for operating the X-ray CT apparatus, or the transfer timing for transferring the data from the buffer to the storage circuitry, which is in a relay circuitry configured to relay communication between the buffer and the console.

14. A data transfer method comprising:
storing data detected by an X-ray detector in a buffer configured to temporarily store therein the data;
acquiring information about residual capacity of the buffer before a scan indicated by a scan plan is performed; and
determining a transfer timing of the data from the buffer to a storage circuitry based on the scan plan and the information about the residual capacity of the buffer.

15. The X-ray CT apparatus according to claim 1, wherein the processing circuitry is further configured to specify the scan by which the data transferred from the buffer is acquired based on a first identifier identifying the scan given to the data that is acquired by each scan in the scan plan of the plurality of scans.

16. The X-ray CT apparatus according to claim 15, wherein the processing circuitry is further configured to designate the first identifier identifying each scan in the scan plan.

17. The X-ray CT apparatus according to claim 16, wherein the processing circuitry is further configured to designate an order of the scans in the scan plan as the first identifier.

18. The X-ray CT apparatus according to claim 16, wherein the processing circuitry is further configured to:
designate a second identifier identifying the scan plan, and
transfer the data, the first identifier, and the second identifier in association with each other.

19. The X-ray CT apparatus according to claim 16, wherein the processing circuitry is further configured to transfer the data in an order different from an order of the scan plan.

20. The X-ray CT apparatus according to claim 16, wherein the processing circuitry is further configured to cause, when an interrupt of a scan plan occurs after an order of transferring the data is determined based on the scan plan, data of the scan plan as an interruption target to be transferred earlier.

21. The X-ray CT apparatus according to claim 16, wherein the processing circuitry is further configured to issue a notification of, when receiving a notification to suspend transfer of the data, a particular first identifier and a particular second identifier indicating data that has been completely transferred.

22. A data transfer method, comprising:
storing data detected by an X-ray detector in a buffer configured to temporarily store therein the data;
determining an order of a unit-of-scan-based transferring of the stored data according to a transfer time of the data, the data being acquired by each scan of a scan plan including a plurality of scans; and
specifying a scan by which the data transferred from the buffer is acquired based on a first identifier given to each scan in the scan plan.

23. An X-ray CT apparatus, comprising:
a buffer configured to temporarily store therein data detected by an X-ray detector; and
processing circuitry configured to
acquire information about residual capacity of the buffer before a scan indicated by a scan plan constituted of a plurality of scans is performed,
determine a transfer timing of the stored data from the buffer to a storage circuitry based on the scan plan and the acquired information about the residual capacity of the buffer, and
control transfer of the data in units of a scan, the data being acquired by each scan of the scan plan.

* * * * *